United States Patent [19]

Masterson et al.

[11] Patent Number: 5,392,766
[45] Date of Patent: Feb. 28, 1995

[54] SYSTEM AND METHOD FOR CLEANING VIEWING SCOPE LENSES

[75] Inventors: Steven Masterson, San Francisco; William R. Dubrul, Redwood City, both of Calif.

[73] Assignee: Innerdyne Medical, Inc., Mountain View, Calif.

[21] Appl. No.: 132,544

[22] Filed: Oct. 6, 1993

[51] Int. Cl.⁶ .................................................. A61B 1/00
[52] U.S. Cl. .................................. 128/4; 15/244.1; 604/264
[58] Field of Search ............... 128/4, 6; 604/1, 264; 15/210.1, 214, 220.4, 244.1

[56] References Cited

U.S. PATENT DOCUMENTS

| | | | |
|---|---|---|---|
| 4,177,814 | 12/1979 | Knepshield et al. | 128/348 |
| 4,517,702 | 5/1985 | Jackson | 15/114 |
| 4,543,751 | 10/1985 | Alikhan | 51/181 R |
| 4,646,722 | 3/1987 | Silverstein et al. | 128/4 |
| 4,656,999 | 4/1987 | Storz | 128/4 |
| 4,682,585 | 7/1987 | Hiltebrandt | 128/4 |
| 4,683,874 | 8/1987 | Acquista | 128/6 |
| 4,760,838 | 8/1988 | Fukuda | 128/4 |
| 4,841,952 | 6/1989 | Sato et al. | 128/6 |
| 4,919,113 | 4/1990 | Sakamoto et al. | 128/4 |
| 4,943,280 | 7/1990 | Lander | 604/169 |
| 5,053,016 | 10/1991 | Lander | 604/169 |
| 5,127,909 | 7/1992 | Shichman | 604/165 |
| 5,183,464 | 2/1993 | Dubrul et al. | 128/3 |
| 5,207,213 | 5/1993 | Auhll et al. | 128/6 |
| 5,274,874 | 1/1994 | Lerione et al. | 15/244.1 |
| 5,304,143 | 4/1994 | Green et al. | 604/167 |

FOREIGN PATENT DOCUMENTS 0497347 8/1992 European Pat. Off. .

Primary Examiner—Richard J. Apley
Assistant Examiner—Beverly A. Meindl
Attorney, Agent, or Firm—Townsend and Townsend Khourie and Crew

[57] ABSTRACT

Percutaneous access devices are provided with cleaning elements for in situ cleaning of viewing scope lenses during surgical procedures. The access devices will comprise a cannula having an access lumen therethrough. The cleaning element will be disposed at or near the distal end of the cannula, preferably over or across a distal port of the cannula. The cleaning element may comprise an elastomeric membrane, an open cell foam pad, one or more articulated plates, or a combination thereof. Cleaning of the lens of the viewing scope is effected by moving the lens between positions proximal of and distal to the cleaning element.

35 Claims, 8 Drawing Sheets

SYSTEM AND METHOD FOR CLEANING VIEWING SCOPE LENSES

BACKGROUND OF THE INVENTION

1. Field of the Invention

The present invention relates generally to the construction and use of percutaneous access devices in performing laparoscopic and related endoscopic surgical procedures. More particularly, the present invention relates to a device and method for in situ cleaning of laparoscopes and other viewing scopes used in such surgical procedures.

Laparoscopic and other endoscopic surgical procedures rely on percutaneous introduction of a viewing scope into an internal region within the patient where the surgical procedure is to be performed. In the case of laparoscopic procedures, the viewing scope is commonly referred to as an endoscope or a laparoscope, and the laparoscope is commonly introduced through an access tube, such as a trocar, which passes into the patient's abdomen. The abdomen will have been insufflated to provide a working region. Using a laparoscope introduced through a trocar, the surgeon can view the region to be treated on a video monitor and can perform a variety of surgical procedures using specialized surgical instruments which are introduced percutaneously either directly or through trocars or other access tubes. Exemplary procedures which may be performed laparoscopically include cholecystectomy, hysterectomy, gastrostomy, appendectomy, bowel resection, herniorrhaphy, and the like. Analogous surgical procedures may be performed elsewhere in the body using other conventional viewing scopes, such as endoscopes, arthroscopes, thoracoscopes, bronchioscopes, hysteroscopes, choledochoscopes, cystoscopes, resectoscopes, and the like.

In all such procedures which employ internally-introduced viewing scopes, problems can arise with fogging and fouling of the distal lens of the scope which provides the optical access. The most common approach for dealing with such obscuring of the distal lens has been to remove the viewing scope and to manually clean it. For example, commercial products are available comprising a sponge or fabric pad and a bottle of cleaning solution. The surgeon can saturate the sponge with the cleaning solution, and clean the distal lens by removing the viewing scope from the patient, wiping the distal lens against the sponge, and returning the viewing scope to the patient. While effective, the need to withdraw the viewing scope from the patient, clean it, reinsert it, and relocate the target, is highly inefficient and inconvenient.

It has also been proposed to incorporate a spray wash nozzle on the viewing scope itself in order to permit cleaning of a distal lens without removing the scope from the patient. While addressing the needs of efficiency, the requirement of incorporating a washing system in the viewing scope itself does not permit cleaning of existing viewing scopes which are already in use. Such viewing scopes can be relatively expensive, limiting the ability to replace such scopes with models incorporating a wash system. Moreover, incorporation of at least one additional lumen and associated hardware for the wash system further complicates construction of the viewing scope, making it more expensive and requiring a larger diameter. Additionally, washing of a distal lens while the viewing scope is in place will not always be effective in cleaning the lens. Many times, it will still be necessary to withdraw the viewing scope to actually wipe the lens clean.

For these reasons, it would be desirable to provide alternative devices and methods for cleaning surgical viewing scopes in situ, i.e., without the need to remove the viewing scope from the patient. Such devices and methods should not require the modification of the viewing scope in any manner, and should preferably require minimum or no modification of other instruments used in performing the surgical procedure, e.g., trocars used for introducing the viewing scope. Such devices and methods should be very effective in removing contaminating debris and fogging of the distal lens of the viewing scope, should be convenient to use, and should be low-cost to implement. Some or all of these objectives will be met by the various embodiments of the present invention described hereinafter.

2. Description of the Background Art

U.S. Pat. No. 4,656,999, describes a contact endoscope having a slidable blade for severing tissue at its distal end. EP 497 347 describes a laparoscope having a lens washing nozzle at its distal end. Scope washing systems are also described in U.S. Pat. Nos. 5,207,213; 4,841,952; 4,760,838; and 4,646,722. U.S. Pat. No. 4,684,874, describes a dissolvable membrane which covers an endoscope lens to protect the lens while being inserted into a patient. U.S. Pat. No. 4,682,585, discloses an endoscope having annular depressions intended to remove contaminants while passing through a trocar. U.S. Pat. No. 4,919,113, describes a spray cleaner for an endoscope. U.S. Pat. No. 4,177,814, describes a self-sealing cannula having an elastomeric valve at its proximal end. Dexide, Fort Worth, Tex., sells a fog reduction/elimination device (FRED) which comprises a sponge and a bottle of cleaning solution, where a scope is removed from the patient to permit cleaning by the sponge. U.S. Pat. Nos. 5,127,909; 5,053,016; and 4,943,280, describe trocar assemblies having flapper valves at their proximal ends for sealing against insufflation pressure. A radially expanding dilator which can incorporate the cleaning assembly of the present invention is described in U.S. Pat. No. 5,183,464.

SUMMARY OF THE INVENTION

The present invention provides apparatus and methods for in situ cleaning of medical viewing scope lenses in order to clear contamination and to inhibit fogging of the lenses, e.g., by applying an anti-fogging solution, during use in surgery and other medical procedures. Devices according to the present invention comprise a cleaning element which is located within or at the end of an access lumen of a cannula or sheath (which may optionally serve as a percutaneous access device) so that a distal lens of the viewing scope engages a cleaning surface of the cleaning element each time it is passed through the access device into the patient. By locating the cleaning element at or near a distal end of the access lumen of the cannula or sheath, the lens can be cleaned simply by partially withdrawing the viewing scope (or otherwise axially translating the scope relative to the cannula) so that the distal lens lies proximal to the cleaning element and thereafter reintroducing the scope past the cleaning element. In this way, the lens engages the cleaning surface of the cleaning element and is wiped clean. Thus, such cleaning can be easily accomplished without the need to remove the viewing scope from the patient.

In a first embodiment of the apparatus of the present invention, the cleaning element is located in a cleaning tube which is insertable into the access lumen of a standard trocar, or dilator device. The cleaning tube will preferably be a thin-walled structure so that it is able to provide An access lumen having only a slightly smaller diameter than that provided by the percutaneous access device itself (thus permitting introduction of conventionally-sized viewing-scopes). The cleaning element will be secured on or within the cleaning tube at or near the distal end thereof. Preferably, the cleaning surface of the cleaning element will extend entirely across the lumen of the cleaning tube so that the viewing scope lens will directly engage the cleaning surface as it is pushed past the cleaning element and into the patient. This first embodiment employing the separate cleaning tube is advantageous since it requires no modification of either the viewing scope or the percutaneous access device, and cleaning tubes can be constructed to be usable with a wide variety of conventional viewing scopes and access devices.

In a second embodiment of the apparatus of the present invention, the cleaning element is located directly in or on a percutaneous access device. The cleaning element will be located so that a cleaning surface thereof extends across the percutaneous access lumen of the access device so that the distal lens of the viewing scope will be cleaned as the scope is introduced through the access device. An advantage of the second embodiment is that no separate component is required for cleaning of the viewing scope. The second embodiment, however, requires using a modified trocar, dilator, or other access device.

In a third embodiment, the cleaning element is disposed in a sheath which covers a viewing scope, such as a flexible endoscope used for gastrointestinal procedures. Such endoscopes are generally used without any type of trocar or other access device, and the sheath of the present invention will have sufficient column strength to support the cleaning element and permit axial translation of the endoscope relative to the cleaning element. In this way, the distal lens of the endoscope can be cleaned without the need to withdraw the scope entirely from the patient. This will be a particular advantage with lengthy scopes where from 100 cm to 200 cm may be in place at the time cleaning becomes necessary.

With any of the embodiments, the cleaning element can take a variety of forms. A first exemplary cleaning element comprises a resilient membrane, usually formed from an elastomeric material, located over a distal port of either the access device, cleaning tube, cannula, or sheath. The cleaning surface is then defined by a cleaning pad located on the proximal side of the resilient membrane. The membrane and cleaning pad are slit to permit passage of the viewing scope therethrough. Usually, the cleaning pad will be an open cell foam and will further be impregnated with a cleaning solution. In this way, the viewing scope will be cleaned each time it passes through the cleaning pad into the patient. The user may also rotate the lens against the cleaning element to remove more adherent substances, in which case it will be desirable for the cleaning element to display some resistance to passage of the lens so that the lens can be pushed against the cleaning element while rotating. A second embodiment of the cleaning element will employ one or more articulated plates mounted at the distal end of the access tube or cleaning tube. The plate will usually also include a cleaning pad formed on its interior (proximal)surface so that the cleaning pad can wipe and clean the distal end of the viewing scope as it is introduced.

While the cleaning element will often be mounted at the distal-most end of the access tube or cleaning tube, it will be appreciated that the cleaning element may be recessed some distance within the access tube or cleaning tube. Such recession, however, will usually be less than 5 cm, preferably being 2 cm or less, since it is desired to limit the distance that the viewing scope needs to be withdrawn in order to effect cleaning. A cleaning element at the proximal end of the access tube or cleaning tube would be ineffective since it would require that the viewing scope be entirely withdrawn from the access tube in order to effect cleaning.

DESCRIPTION OF SPECIFIC EMBODIMENTS

Figure 1:
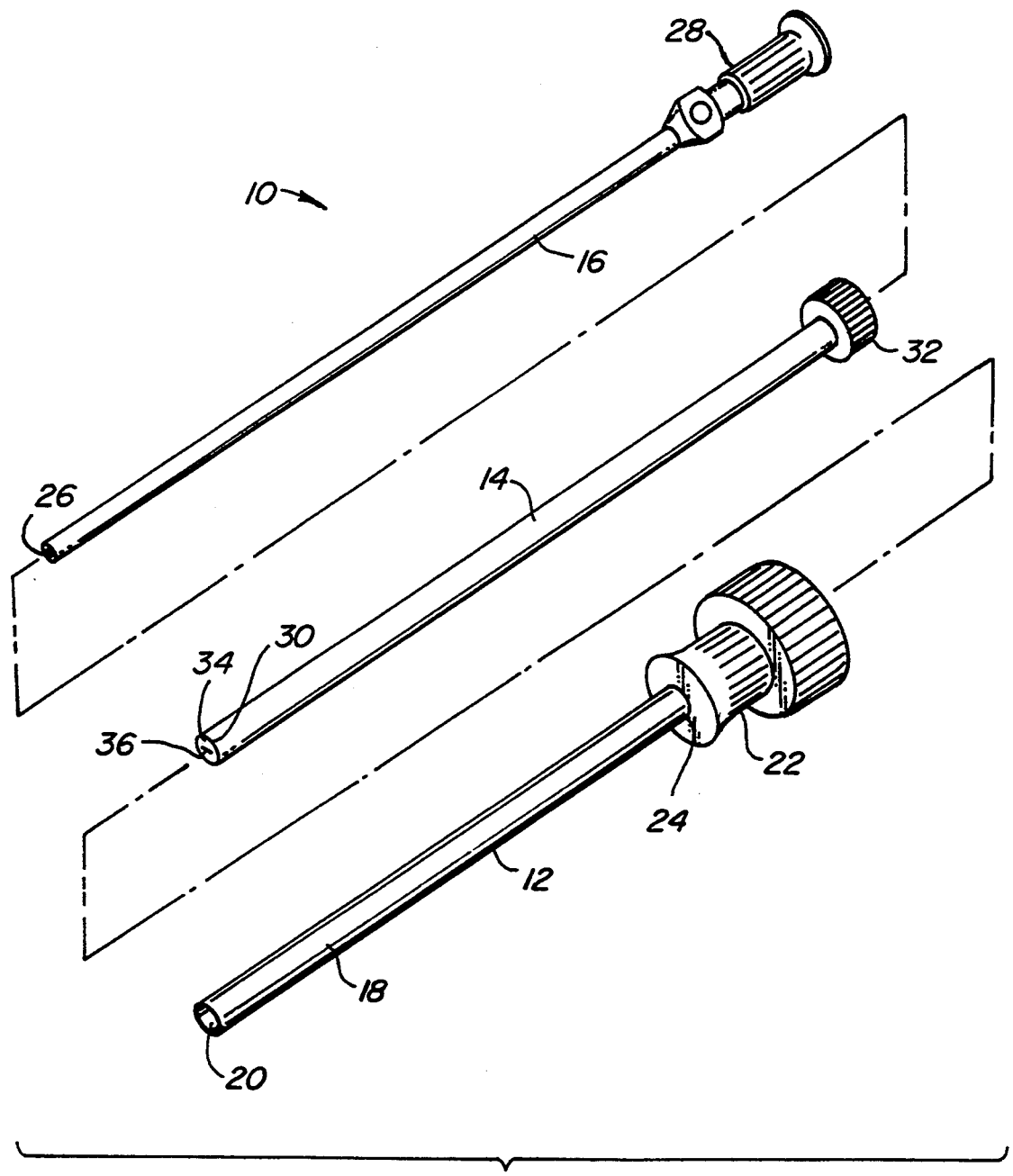
FIG. 1 illustrates a percutaneous access system constructed in accordance with the principles of the present invention and including a separate cleaning tube.

The present invention provides apparatus and methods for cleaning lenses located at the distal ends of medical viewing scopes during use in surgical procedures. The present invention can be used with a wide variety of viewing scopes, often referred to generally as endoscopes, and more particularly being referred to as laparoscopes, arthroscopes, thoracoscopes, bronchioscopes, hysteroscopes, choledochoscopes, cystoscopes, resectoscopes, and the like, depending on the particular type of surgical procedure being employed. The present invention is most particularly useful with the cleaning of laparoscope lenses during laparoscopic procedures where the laparoscope is introduced into the insufflated abdominal region of a patient in order to perform a surgical procedure, such as cholecystectomy, hysterectomy, gastrostomy, appendectomy, bowel resection, herniorrhaphy, and the like. In such cases, the present invention will be able to both remove particulate and other contamination which may physically coat the lens as a result of the procedure being performed, as well as apply an anti-fogging solution to the lens in order to inhibit condensation on the lens as a result of the introduction of a relatively cold lens into a warm, moist environment.

Laparoscopic and other least invasive surgical procedures are generally performed through small percutaneous incisions in the patient's abdomen or elsewhere, depending on the particular procedure being performed. Such incisions are frequently created using self-introducing trocars which are commercially available from a number of suppliers, such as United States Surgical Corporation, Norwalk, Conn.; Ethicon Endosurgical, Inc., Cincinnati, Ohio; Dexide, Fort Worth, Tex.; Origin Medsystems, Inc., Menlo Park, Calif.; and Applied Medical Resources, Laguna Hills, Calif. Such trocars provide an access sheath or a cannula having an access lumen therethrough to permit introduction of the viewing scope and/or other appropriately-sized surgical instruments. In the case of laparoscopic procedures, where the patient's abdomen is insufflated, the trocars will necessarily include a valve or other sealing element at their proximal ends in order to prevent the release of the pressurized gases. Other procedures, such as arthroscopic and thoracoscopic procedures, may not require sealing valves or other mechanisms. The methods and devices of the present invention, in one aspect, will be designed to be compatible with, or to modify, standard trocars of the type which are now available. Such standard trocars are also well described in the patent literature. See, for example, U.S. Pat. Nos. 5,127,909; 5,053,016; 4,943,280; and 4,177,814, the full disclosures of which are incorporated herein by reference.

The present invention is also compatible with other percutaneous access devices, such as sheaths, dilator tubes, and the like, which can be introduced in a known manner to form and thereafter increase the diameter of percutaneous penetrations through the abdomen and elsewhere. A particularly preferred dilator is the radially expandable dilator, as described in U.S. Pat. No. 5,183,464, the full disclosure of which is incorporated herein by reference.

Use of the present invention, however, is not limited to conventional trocars and/or dilator, but instead can be used with any device or apparatus comprising an elongate, tubular structure having an axial lumen which in turn provides access into a patient body region where it is desired to perform a surgical procedure using a medical viewing scope. In that case, the access tube can be modified or used together with a viewing scope cleaning tube, as described in more detail hereinafter. The present invention is also useful with other viewing scopes which do not require an access device, i.e., which may be introduced through a natural body orifice such as the mouth, nose, ear, anus, vagina, urethra, and the like. In such cases, a sheath, cannula, or other exterior structure can be provided for the specific purpose of carrying a cleaning element and permitting the distal lens of the viewing scope to be axially translated to wipe against the cleaning element. For convenience, all tubular support structures will be collectively referred to as cannulas hereinafter and in the claims. Thus, the term "cannula" is intended to refer to trocars, sheaths, dilators, and any other outer structure which can support a cleaning element over a viewing scope so that a lens of the scope can be cleaned on the cleaning element, as described hereinafter.

The present invention functions by providing a cleaning element within the access lumen of the percutaneous access device, e.g., trocar, dilator, or other access tube or sheath. The cleaning element may be mounted directly in or on the access device, or may be part of a separate cleaning tube structure which is removably inserted into the access device (where the access device passes directly through the patient's skin into the region of interest). Alternatively, the cleaning element may be provided on a separate support sheath or structure which is intended solely for supporting the cleaning element and which serves no other purpose. Such separate support structures will be partricularly useful with endoscopes which are introduced without a specialized access device. In any case, in use, the cleaning element will be disposed near the distal end of the access lumen of the percutaneous access device sheath, or other support structure, so that the lens or other distal optical elements of the viewing scope will engage a cleaning surface of the cleaning element as the viewing scope is introduced through the access lumen in a distal direction past the cleaning surface of the cleaning element.

The cleaning surface may have a wide variety of structures. In a simple case, the cleaning surface may be one side of an elastomeric membrane having a slit therethrough, where the surface of the membrane is expanded and dilated as the viewing scope is passed therethrough. As the slit is expanded, the edges of the slit will wipe over the distal lens or other optical element of the viewing scope to remove debris, condensation, contaminants, and other material which may be present on the lens and obscuring visual access. Frequently, it will be desirable to provide an absorptive cleaning pad, either with the elastomeric membrane or in place of the elastomeric membrane. The cleaning pad will frequently be an open cell foam which can be impregnated or saturated with a suitable cleaning solution, such as a mild, physiologically compatible detergent. Such open cell foam structures can also be provided with one or more slits in order to facilitate passage of the viewing scope therethrough. As with the elastomeric membrane, the open cell foam will expand to permit passage and will wipe off and clean the lens or other optical element as it opens. The foam will also be able to apply the cleaning solution to the surface of the lens in order to clean and anti-fog the lens. The cleaning pad will also offer sufficient resistance to passage of the viewing scope so that the user can feel when contact is first made. The user Can thus engage the lens of the viewing scope against the cleaning element and rotate or otherwise scrub the lens against the cleaning element to thoroughly clean it. Other structures of the cleaning element may employ articulated plate(s), usually having an open cell foam mounted on a proximal surface thereof. Such articulated structures can be advantageous since they can be designed to more readily move out of the way of the viewing scope as the viewing scope is introduced therethrough. In this way, the available area through the cleaning tube or percutaneous access device itself can be maximized.

The cleaning tube of the present invention will be an elongate structure capable of being inserted into a conventional trocar, dilator, or other percutaneous or nonpercutaneous access device. The cleaning tube will be designed to occupy,as little area of the access lumen of the access device as possible, i.e., it will not increase the effective diameter of the viewing scope being introduced through the access lumen. Usually, the cleaning tube will be a thin-walled tube formed of metal or plastic, typically having a wall thickness below about 0.02 inches, preferably having a wall thickness below about 0.01 inches other suitable structures include open frameworks, parallel rods, cylinders having cut-out walls, and the like. A variety of structures will be sufficient so long as they permit insertion through the access lumen and support of the cleaning element at or near the distal end thereof.

The dimensions of the cleaning tube will depend primarily on the internal dimensions of the trocar, dilator, or other, access device into which is to be placed, as well as the dimensions of the viewing scope. For example, a conventional 11/12 mm trocar has an inner diameter of about 12.2 mm. In such case, the cleaning tube would have an outer diameter just below 12.2 mm and an inner diameter of almost 12 mm. Such an inner diameter will be more than sufficient to accommodate most commercially available laparoscopes. The length of the cleaning tube will usually be slightly longer than that of the trocar into which it is to be placed. Such longer length, however, is not necessary, since it is possible that the cleaning element will be recessed within the distal end of the access device. Suitable lengths of the cleaning tube will be from 7 to 40 cm, usually from 7 to 25 cm and more usually from 7 to 15 cm.

The cleaning tube may have a valve or sealing assembly mounted on or near its proximal end. Such valves and sealing assemblies are particularly useful when the cleaning tube is to be used with an access device in a laparoscopic procedure. As the cleaning tube provides a separate access lumen, it is desirable that the access lumen be sealed in order to prevent loss of insufflation. In some cases, the cleaning element itself will be sufficient to seal over the laparoscope and prevent loss of insufflation. In other cases, the cleaning element may not provide an effective seal, and it will then be possible to mount conventional sealing valves at the proximal end of the cleaning tube. Such sealing valves are described in the trocar patents previously incorporated herein by reference.

Referring now to FIG. 1, a first exemplary percutaneous access system 10 constructed in accordance with the principles of the present invention will be described. The access system 10 comprises a trocar tube 12, a cleaning tube 14, and a laparoscope 16. The trocar 12 is generally conventional, including an elongate cannula 18 having a distal end 20 and an insufflation valve 22 at its proximal end 24. Similarly, the viewing scope 16 is conventional, having a distal viewing lens 26 and a proximal housing 28 for connection to video monitoring equipment (not illustrated).

The cleaning tube 14 is a separate component of the access system 10 and is insertable axially through the trocar 12. The cleaning tube 14 has a distal end 30, with a distal port 30A a proximal end 32 and a cleaning lumen extending therebetween. It will be appreciated that the cleaning lumen provides access for the laparoscope 16 when it is introduced through the cleaning tube 14.

Cleaning tube 14 further comprises an elastomeric membrane 34 mounted over its and distal port 30A. Membrane 34 includes a transverse slit 36 so that the membrane is expanded as the distal end of the laparoscope 16 passes through. The membrane, as it is expanded, acts to wipe the distal end 26 of the laparoscope free of contamination, condensation, and the like.

Figure 2:
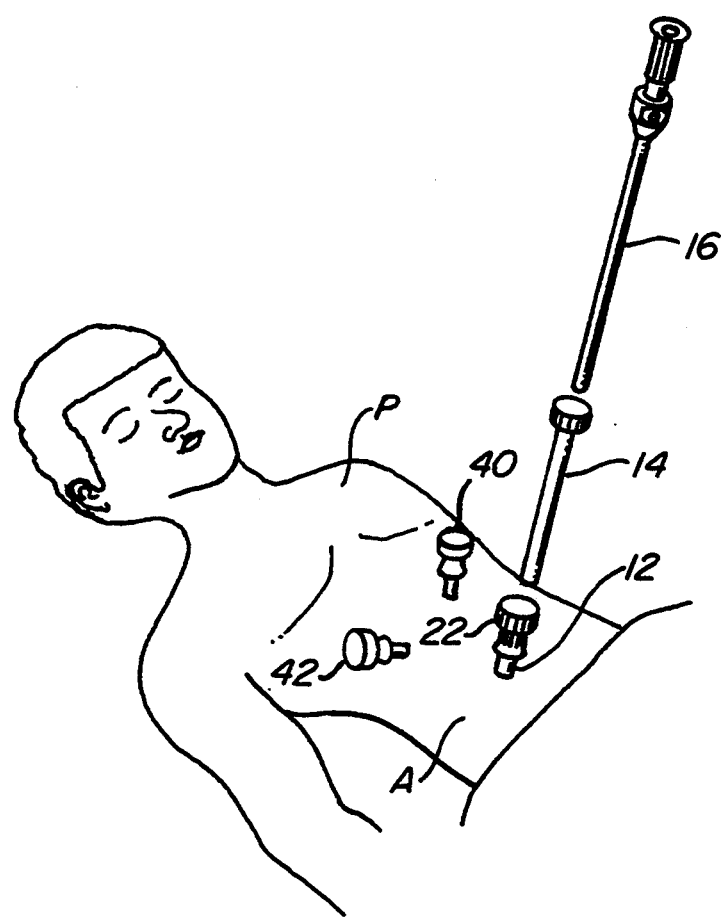
FIG. 2 illustrates generally how the percutaneous access system of FIG. 1 is introduced to a patient during a laparoscopic procedure.

Referring now to FIG. 2, the components of the access system 10 are introduced to a patient P, as illustrated. The trocar 12 is first introduced through the abdominal wall in a conventional manner, typically using a stylet for self-introduction (not illustrated). Thereafter, the cleaning tube 14 will be introduced through the valve structure 22 of the trocar 12. Finally, the laparoscope 16 will be introduced through the cleaning lumen of the cleaning tube 14. In most laparoscopic procedures, other trocars 40 and 42 will be introduced through other regions of the abdomen in order to provide access for surgical instruments in order to perform the desired procedure.

Figure 3:
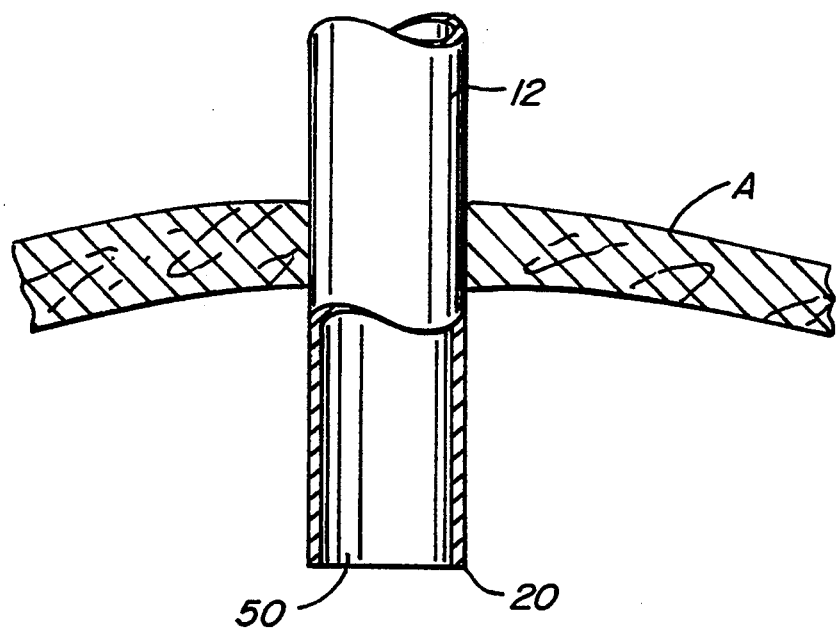
FIGS. 3-5 are detailed views of the distal ends of the components of the system of FIG. 1 shown in use in a procedure penetrating the abdominal wall.
Figure 4:
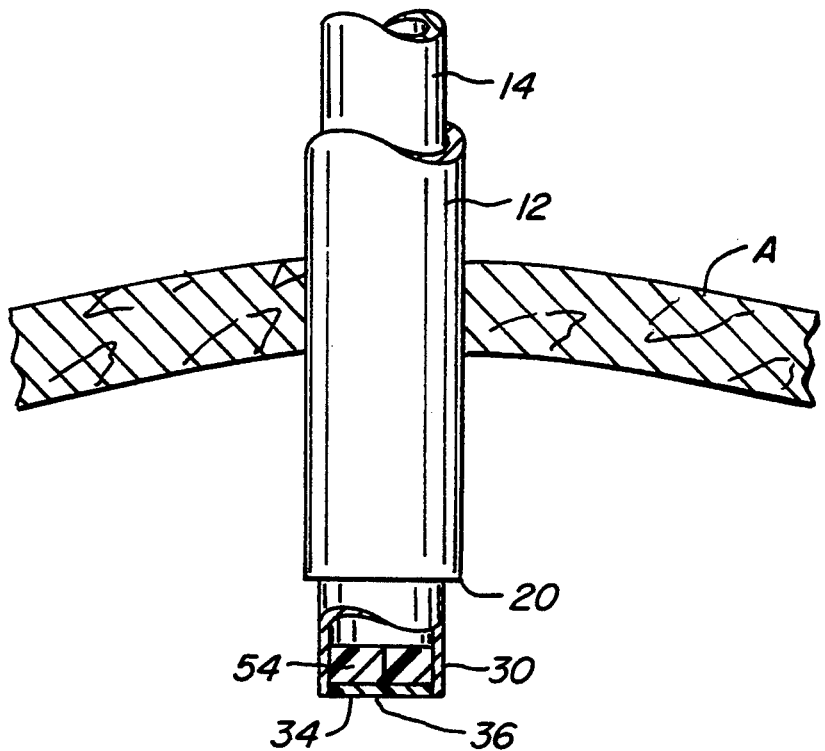
Figure 5:
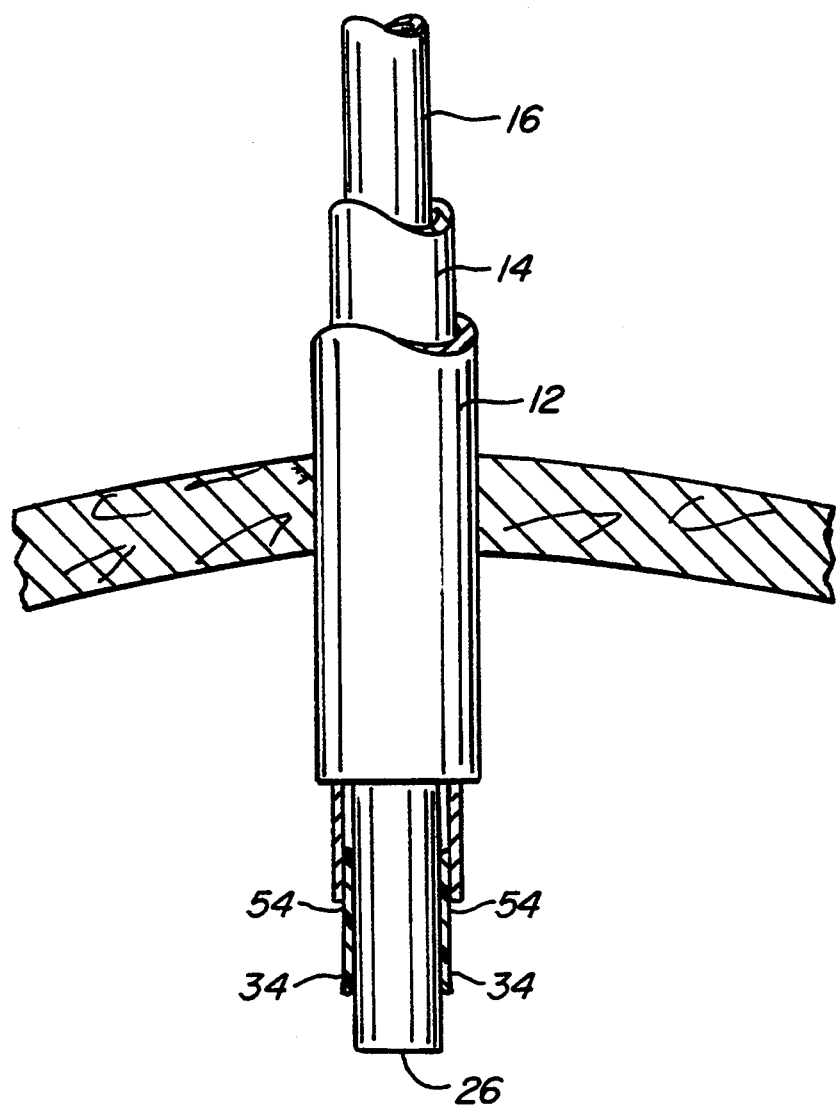

Referring now to FIGS. 3–5, the distal ends of the trocar 12, cleaning tube 14, and laparoscope 16, are illustrated as they are sequentially introduced through the patient's abdomen A. As illustrated in FIG. 3, trocar 12 is in place and has an open distal port 50 which is exposed to the insufflated peritoneum lying beneath the abdomen. It will be appreciated that a source of insufflation will have been provided through at least one of the trocars which has been introduced to the patient in a conventional manner.

As illustrated in FIG. 4, the cleaning tube 14 is next introduced so that the distal end 30 extends distally beyond the distal end 20 of the trocar. During this time, the slit 36 of membrane 34 remains closed to prevent loss of insufflation pressure. An optional foam cleaning pad 54 is illustrated on the proximal side of the membrane 34. The cleaning pad 54 will generally be an open cell foam, and will preferably be impregnated with a cleaning solution, as described previously.

As the laparoscope 16 is introduced through the cleaning tube 14, as illustrated in FIG. 5, the membrane 34 and cleaning pad 54 will be opened outward, with the inner or proximal surface of the cleaning pad 54 wiping across the distal ends 26 of the laparoscope. Thus, the inner surface of the cleaning pad 54 acts as the cleaning surface of the present invention.

During the laparoscopic procedure, whenever the distal ends 26 becomes contaminated with debris, fog, or other obscuring matter, the physician may clean the lens simply by drawing the laparoscope in a proximal direction, i.e., out from the patient, so that the lens enters into the interior of the cleaning tube 14. The membrane 34 and/or foam 54 close, generally as illustrated in FIG. 4. The lens 26 can then be cleaned by simply reinserting the laparoscope so that the lens once again passes through the cleaning element comprising the membrane 34 and foam cleaning pad 54. Such a cleaning operation can be-repeated as often as desired to keep the lens clean.

Figure 6:
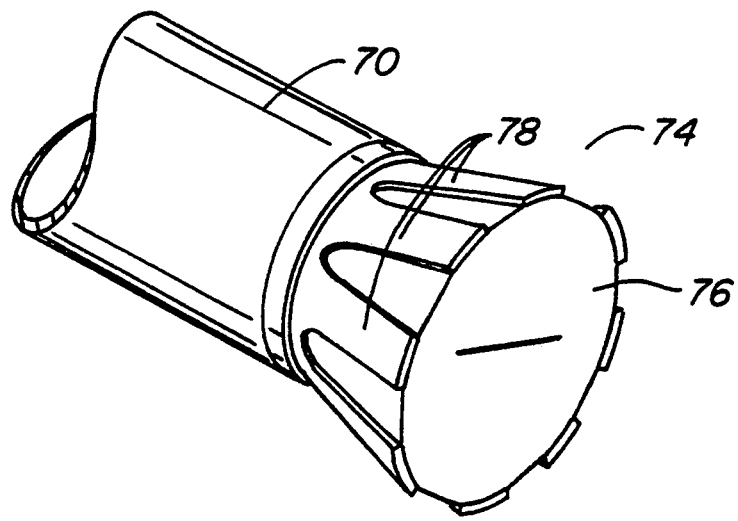
FIG. 6 illustrates an alternative embodiment of the cleaning tube of the system of FIG. 1, having an expandable distal tip.
Figure 7:
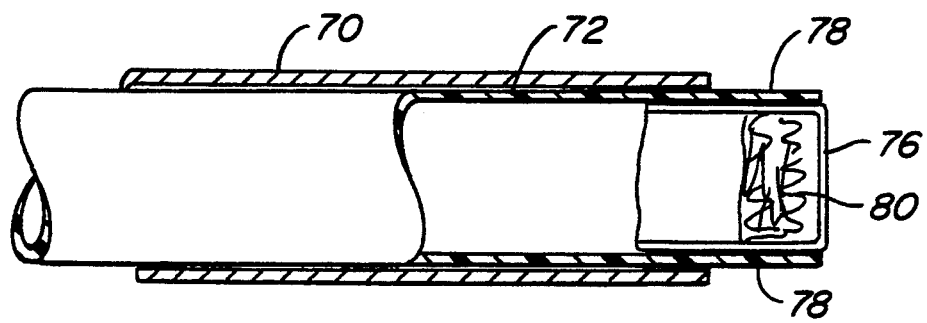
FIGS. 7 and 8 are cross-sectional views of the embodiment of FIG. 6, showing the distal end in its collapsed and expanded configurations, respectively.
Figure 8:
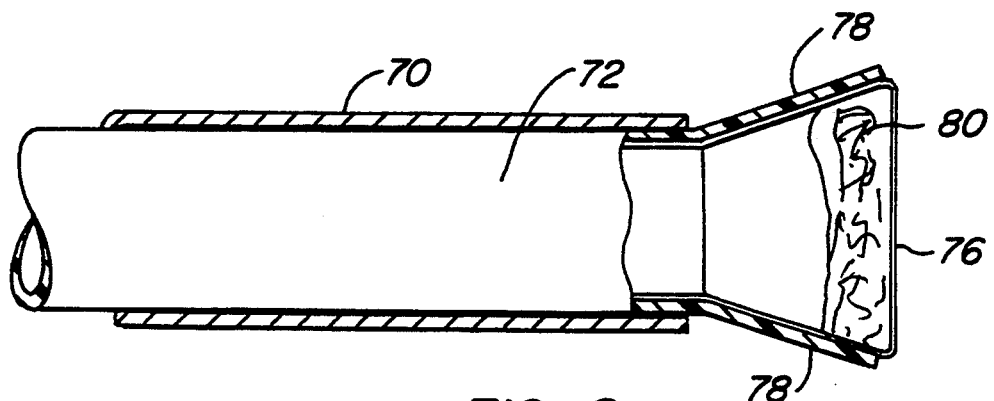

Referring now to FIGS. 6–8, an alternative embodiment of the cleaning tube of the present invention is illustrated. These Figures illustrate only the distal tip of the trocar and cleaning tube. It will be appreciated, however, that the proximal ends will be generally as described previously in connection with FIG. 1.

Trocar 70 comprises a cannula having an open distal end, which is generally identical to that illustrated in FIG. 1. The cleaning tube 72, however, comprises an expandable distal tip having a membrane 76 extending thereacross. The expandable tip comprises a plurality of resilient fingers or slats which form a distal extension of the cleaning tube 72. Conveniently, the fingers 78 may be formed integrally with the cleaning tube 72, with expansion being provided by forming integral spring joints in the wall of the tube. Thus, when the cleaning tube 72 is sufficiently withdrawn within the trocar 70, the distal tip will be in a collapsed configuration, as illustrated in FIG. 7. When the cleaning tube 72 is extended distally outward from the trocar 70, as illustrated in FIGS. 6 and 8, the tip springs open to assume its expanded configuration. In the expanded configuration, the membrane 76 is stretched and extra volume is provided immediately behind the membrane. Optionally, an open cell foam cleaning pad 80 (having a slit to permit passage of the viewing scope) may be disposed within this expanded region. The laparoscope will pass through the cleaning pad 80 and membrane 76 in a manner analogous to that illustrated in FIGS. 3-5. The advantage of the expanded tip configuration is that there is no loss of internal access diameter. That is, in the embodiment of FIG. 1, the cleaning pad 54 occupies a discrete annular region within the cleaning tube 14, even when the laparoscope is inserted therethrough. Thus, the maximum size of the laparoscope is limited by the need to allow for clearance of the cleaning pad 54 and membrane 34. The embodiment of FIGS. 6-8, by providing the expanded volume behind membrane 76, allows the use of laparoscopes which are as large as the internal diameter of the cleaning tube 72 itself.

Figure 9:
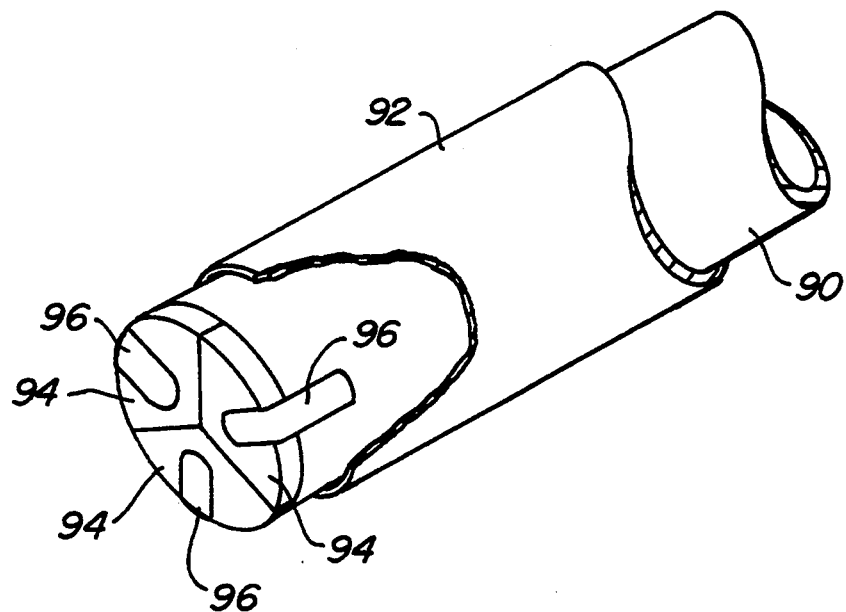
FIGS. 9 and 10 illustrate a second alternative embodiment of the cleaning tube of the system of FIG. 1, employing a plurality of articulated plates having attached cleaning pads, shown in a closed configuration and an open configuration, respectively.
Figure 10:
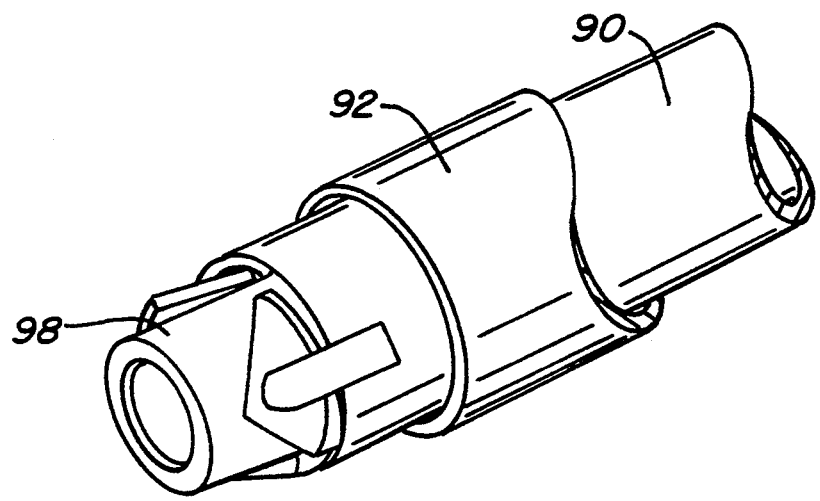

Referring now to FIGS. 9 and 10, a cleaning tube embodiment employing articulated or hinged cleaning plates is illustrated. The cleaning tube 90 is mounted in a trocar 92, in a manner analogous to that illustrated in the system of FIG. 1. Three articulated cleaning plates 94 are mounted at the distal end of the cleaning tube 90, being pivotally attached with hinges 96. As can be seen in FIG. 10, as laparoscope 98 is passed through the cleaning tube 90, the articulated plates 94 are swung completely out of the way so that laparoscopes having an external diameter substantially equal to that of the internal diameter of the cleaning tube may be employed. In a preferred embodiment, the hinge structures 96 will be formed from a superelastic alloy, such as a nickel-titanium alloy, such as Nitinol®. In this way, as the laparoscope is passed proximally back into the cleaning tube 90, the hinged plates 94 will close, as illustrated in FIG. 9.

Figure 11:
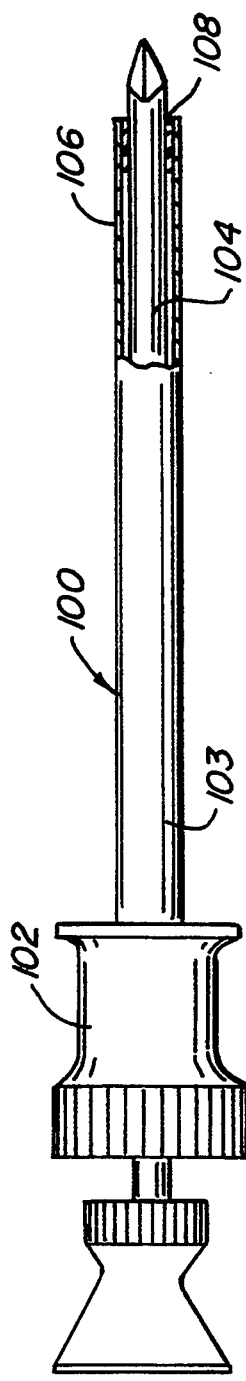
FIGS. 11-13 illustrate a second embodiment of the percutaneous access system of the present invention, comprising a trocar having a cleaning element mounted directly within its distal end.
Figure 12:
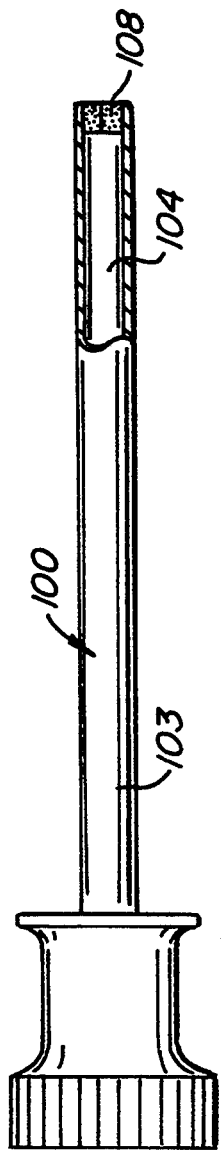
Figure 13:
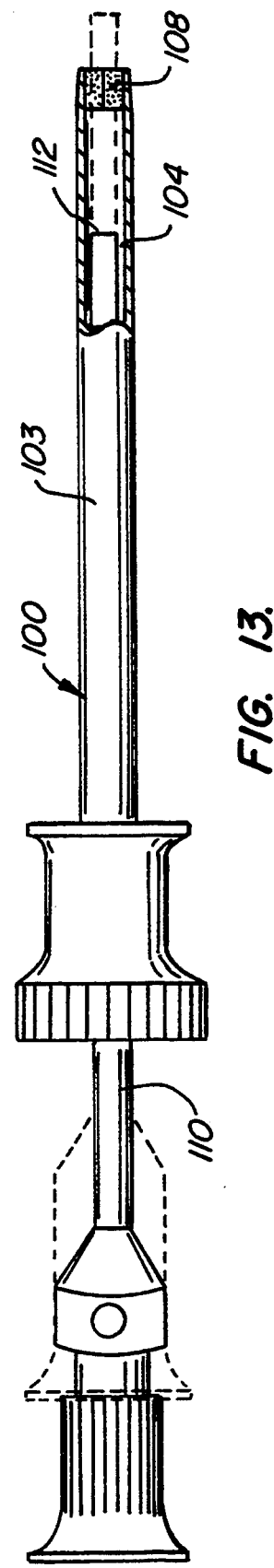

As discussed thus far, all of the embodiments of the present invention have employed separate cleaning tubes intended for insertion through conventional trocars, dilator, or other percutaneous access devices. The present invention, however, is not limited to the use of such separate cleaning tubes, and can instead provide for incorporation of a cleaning element directly in an otherwise conventional trocar, dilator, or other percutaneous access device. Such an alternative embodiment is illustrated in FIGS. 11-13. In FIG. 11, trocar 100, having a conventional trocar valve 102 at its proximal end of cannula 103, is illustrated with self-introducing stylet 104 mounted in access lumen 106 thereof. According to the present invention, a resilient cleaning pad 108 is mounted at the distal end of the trocar. The cleaning pad is outwardly radially compressed by the stylet. In this way, the stylet can extend distally from the distal end of the trocar to permit self-introduction in a conventional manner.

After the trocar 100 has been introduced, the stylet 104 will be removed, allowing the resilient cleaning pad 108 to expand radially inward and assume a closed configuration, as shown in FIG. 12.

As illustrated in FIG. 13, after the stylet 104 has been removed, a conventional laparoscope 110 can be introduced through the access lumen 104 of the trocar 100. The distal end 112 of the laparoscope, having a distal lens thereon, approaches the resilient cleaning pad 108, as illustrated in full line. The laparoscope may then be pushed past the cleaning pad 108, as illustrated in broken line. The lens on the laparoscope 110 may thereafter be cleaned by simply moving the laparoscope between the positions shown in broken line and full line, so that the lens is wiped against the cleaning pad. If needed during the procedure, the cleaning pad 108 may be replenished with cleaning fluid using a swab or syringe to introduce the solution.

Although FIGS. 11-13 illustrate a conventional trocar, it will be appreciated that the cleaning element of the present invention may also be incorporated in dilators, e.g., as described in U.S. Pat. No. 5,183,464, as well as virtually any other percutaneous access device which is intended to receive a medical viewing scope therethrough.

Figure 14:
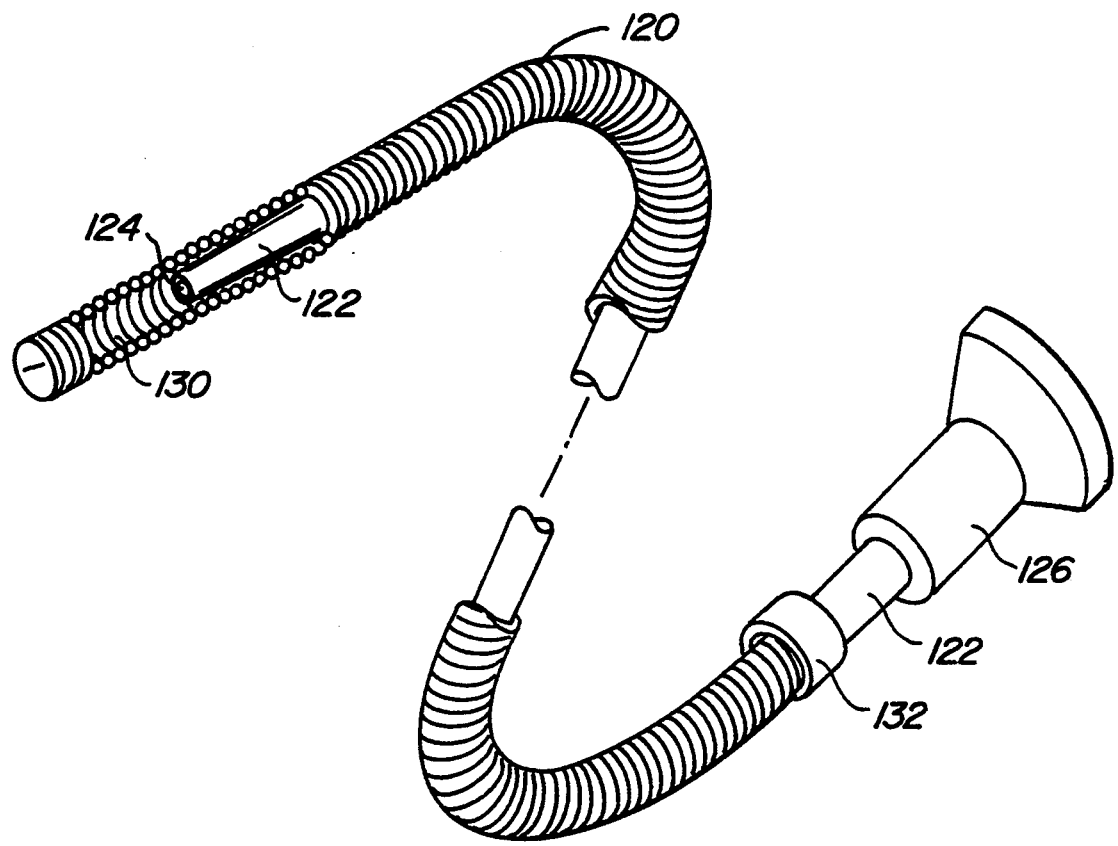
FIGS. 14-16 illustrate a third embodiment of the apparatus of the present invention comprising a sheath disposed over a flexible endoscope of the type useful for gastrointestinal viewing.
Figure 15:
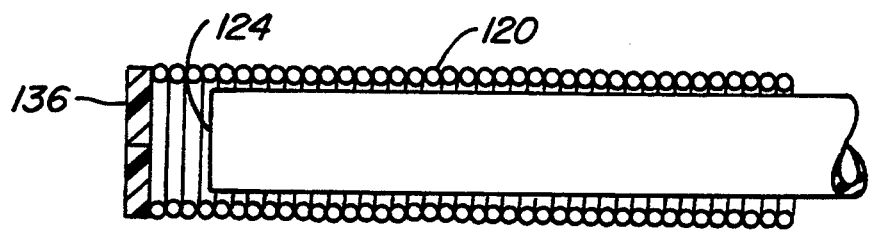
Figure 16:
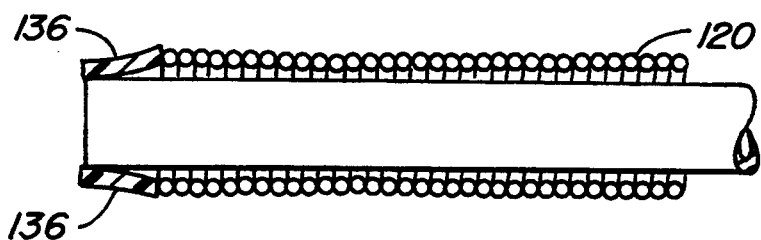

FIGS. 14-16 illustrate a third embodiment of the apparatus of the present invention comprising an outer sheath 120 disposed coaxially over a flexible endoscope 122. The endoscope may be any conventional elongate viewing scope having a viewing lens 124 at its distal end and an eyepiece 126 at tis proximal end. The endoscope may also include a variety of other components, such as access lumens, working channels, and the like, but such other features are not illustrated in FIGS. 14-16.

The sheath 120 includes an access lumen 130 extending its entire length, where the access lumen slidably receives the endoscope 122. The length of the sheath will be slightly less than that of the endoscope, and the sheath terminates in a ring 132 at its proximal end. The ring 132 facilitates gripping of the sheath 120 by the user, enabling the user to hold both the sheath and endoscope 122 and slide them relative to each other. In that way, the viewing lens 124 on the endoscope 122 can be passed through cleaning pad 136, as shown in FIGS. 15 and 16.

The sheath 120 may be constructed or composed of any material which is able to provide sufficient column strength to support the cleaning pad 136 and hold the pad while the viewing lens 124 is passed through the cleaning pad. Conveniently, the sheath may be a coil structure, but a variety of other reinforced and non-reinforced materials would also be suitable.

Although the foregoing invention has been described in detail for purposes of clarity of understanding, it will be obvious that certain modifications may be practiced within the scope of the appended claims.

What is claimed is:

1. A scope cleaning device comprising:
   a cannula having a proximal end, a distal end having a distal port, and a lumen therethrough; and
   a cleaning element secured to the cannula near the distal end, said cleaning element having a cleaning surface which is disposed across the distal port so that passage of a viewing scope having a distal lens through the lumen will engage and wipe the distal lens against the cleaning surface as the distal lens passes through the port.

2. A device as in claim 1, wherein the cleaning element is an elastomeric membrane having a cleaning pad attached to an interior surface thereof.

3. A device as in claim 2, wherein the cleaning pad is an open cell foam impregnated with a cleaning solution.

4. A device as in claim 1, wherein the cleaning element comprises one or more hinged plates having a cleaning pad attached to an interior surface thereof.

5. A device as in claim 4, wherein the cleaning pad is an open cell foam impregnated with a cleaning solution.

6. A device as in claim 1, wherein the cleaning element is secured over the distal end of the cannula so that it entirely covers an open distal port of the access lumen.

7. A device as in claim 1, wherein the cleaning element is secured in the lumen within 5 cm of the distal end of the cannula.

8. A device as in claim 1, further comprising a stylet having a tapered distal end which is removably received within the lumen of the cannula, wherein the tapered end extends distally beyond the distal end of the cannula to facilitate percutaneous penetration of the cannula.

9. A viewing scope cleaning assembly for use with a percutaneous access device having a cannula with a proximal end, a distal end, and an access lumen therethrough, said cleaning assembly comprising:
a cleaning tube having a proximal end, a distal end, and cleaning lumen therethrough, wherein said cleaning tube is removably insertable into the access lumen of the percutaneous access device; and
a cleaning element disposed near the distal end of the cleaning tube and having a cleaning surface which is disposed across the cleaning lumen so that passage of a viewing scope having a distal lens through the cleaning lumen will wipe the distal lens against the cleaning surface of the cleaning element.

10. A cleaning assembly as in claim 9, wherein the cleaning element is an elastomeric membrane having a cleaning pad attached to an interior surface thereof.

11. A cleaning assembly as in claim 10, wherein the cleaning pad is an open cell foam impregnated with a cleaning solution.

12. A cleaning assembly as in claim 9, wherein the cleaning element is a hinged plate having a cleaning pad attached to an interior surface thereof.

13. A cleaning assembly as in claim 12, wherein the cleaning pad is an open cell foam impregnated with a cleaning solution.

14. A cleaning assembly as in claim 9, wherein the cleaning element is secured over the distal end of the cleaning tube so that said cleaning element will be located at or near the distal end of the access lumen when the cleaning tube is inserted in the percutaneous access device.

15. A cleaning assembly as in claim 9, wherein the cleaning element is secured in the cleaning lumen within 5 cm of the distal end of the cleaning tube, so that said cleaning element will be located at or near the distal end of the access lumen when the cleaning tube is inserted in the percutaneous access device.

16. A cleaning assembly as in claim 9, further comprising a valve for sealing the cleaning lumen at or near the proximal end of the cleaning tube.

17. An improved percutaneous access device of the type including a cannula having a proximal end, a distal end having a distal port, and an access lumen therethrough, wherein the improvement comprises a cleaning element disposed near the distal end of the cannula and having a cleaning surface extending across the distal port so that passage of a viewing scope having a distal lens through the access lumen will wipe the distal lens against the cleaning surface of the cleaning element as the distal lens of the viewing scope passes through the distal port.

18. An improved percutaneous access device as in claim 17, wherein the improvement further comprises a cleaning tube having a cleaning lumen, which cleaning tube is removably inserted in the access lumen of the cannula, wherein the cleaning element is disposed on the cleaning tube so that the cleaning surface extends across the cleaning lumen.

19. An improved percutaneous access device as in claim 17, wherein the cleaning element is affixed directly on the cannula so that the cleaning surface extends across the access lumen but does not block distal progress of the viewing scope through the distal port.

20. An improved device as in claim 17, wherein the cleaning element is an elastomeric membrane having a cleaning pad attached to an interior surface thereof.

21. A improved device as in claim 20, wherein the cleaning pad is an open cell foam impregnated with a cleaning solution.

22. A improved device as in claim 17, wherein the cleaning element comprises one or more hinged plates having a cleaning pad attached to an interior surface thereof.

23. A improved device as in claim 22, wherein the cleaning pad is an open cell foam impregnated with a cleaning solution.

24. A device as in claim 18, wherein the cleaning element is secured over the distal end of the cleaning tube.

25. A device as in claim 18, wherein the cleaning element is secured in the cleaning lumen within 5 cm of the distal end of the cleaning tube.

26. An improved device as in claim 19, wherein the cleaning element is secured over the distal end of the cannula.

27. A device as in claim 19, wherein the cleaning element is secured in the access lumen within 5 cm of the distal end of the cannula.

28. A method for in situ cleaning of a distal lens on an elongate viewing scope, said method comprising:
introducing the viewing scope through a cannula having a distal port and a cleaning element disposed across the distal port thereof, wherein passage of the distal lens by the cleaning element effects cleaning of the lens.

29. A method as in claim 28, further comprising partially withdrawing the viewing scope from the cannula so that the distal lens passes the cleaning element in a proximal direction and thereafter reintroducing the scope past the cleaning element in a distal direction to effect cleaning, while keeping the viewing scope substantially within the cannula.

30. A method as in claim 28, wherein the cleaning element is integrally incorporated in the cannula which forms part of a trocar or dilator tube.

31. A method as in claim 28, wherein the cleaning element is incorporated in a cleaning assembly which is removably inserted in the cannula which forms part of a trocar or dilator tube.

32. A method as in claim 28, wherein the cleaning element is an elastomeric membrane having a cleaning pad affixed to an interior surface thereof.

33. A method as in claim 28, wherein the cleaning element comprises one or more hinged plates having a cleaning pad affixed to an interior surface thereof.

34. A method as in claim 28, wherein the cleaning element comprises a cleaning pad having a cleaning solution absorbed therein.

35. A method as in claim 28, further comprising rotating the viewing scope about its axis while the distal lens is in contact with the cleaning element.

* * * * *